(12) United States Patent
Melching et al.

(10) Patent No.: US 7,100,396 B2
(45) Date of Patent: Sep. 5, 2006

(54) CLIMATIC CABINET AND, IN PARTICULAR, A CLIMATIC COOLING CABINET

(75) Inventors: Achim Melching, Langenselbold (DE); Olaf Brömsen, Mörfelden-Walldorf (DE); Dieter Bidlingmaier, Bruchköbel (DE); Hermann Stahl, Mühlheim (DE)

(73) Assignee: Kendro Laboratory Products GmbH, Langenselbold (DE)

( * ) Notice: Subject to any disclaimer, the term of this patent is extended or adjusted under 35 U.S.C. 154(b) by 198 days.

(21) Appl. No.: 10/766,900

(22) Filed: Jan. 30, 2004

(65) Prior Publication Data

US 2004/0200227 A1    Oct. 14, 2004

(30) Foreign Application Priority Data

Jan. 30, 2003   (DE)   ............................... 103 03 736

(51) Int. Cl.
*F25D 11/00*   (2006.01)
(52) U.S. Cl. ..................... 62/440; 62/380; 62/419; 454/191; 454/193
(58) Field of Classification Search .............. 62/440, 62/380, 419; 454/190, 191, 193
See application file for complete search history.

(56) References Cited

U.S. PATENT DOCUMENTS

| | | | | |
|---|---|---|---|---|
| 1,819,231 A | * | 8/1931 | Crawford et al. | 34/227 |
| 2,397,726 A | * | 4/1946 | Cook | 432/86 |
| 2,775,187 A | * | 12/1956 | McClurkin | 454/190 |
| 3,387,600 A | * | 6/1968 | Terzian | 126/21 R |
| 3,713,401 A | * | 1/1973 | McClurkin | 432/64 |
| 3,750,622 A | * | 8/1973 | Repp et al. | 118/326 |
| 5,113,749 A | * | 5/1992 | Perbix | 454/193 |
| 5,132,520 A | * | 7/1992 | Blanton et al. | 219/400 |
| 5,169,217 A | | 12/1992 | Orchard et al. | 312/223.1 |
| 5,233,844 A | | 8/1993 | Knippscheer et al. | 62/440 |
| 5,425,793 A | * | 6/1995 | Mori et al. | 55/385.2 |
| 5,461,878 A | * | 10/1995 | Moore et al. | 62/255 |
| 5,765,982 A | * | 6/1998 | Martin et al. | 414/156 |
| 5,876,280 A | * | 3/1999 | Kitano et al. | 454/187 |
| 6,595,429 B1 | * | 7/2003 | Carlson et al. | 236/44 R |
| 2004/0003617 A1 | * | 1/2004 | Chandler et al. | 62/256 |

FOREIGN PATENT DOCUMENTS

| | | |
|---|---|---|
| FR | 2 770 630 | 7/1999 |
| WO | 95/06301 | 3/1995 |

* cited by examiner

*Primary Examiner*—William C. Doerrler
(74) *Attorney, Agent, or Firm*—Baker & Hostetler LLP

(57) ABSTRACT

The invention concerns a climatic cabinet, in particular, a climatic cooling cabinet, whose interior is loaded or unloaded with specimen slides, with the aid of a transporting device. The loading and unloading take place through a loading opening which can be closed with a door, which opening is adapted, in its size, to the dimensions of the specimen slides and is located in a sidewall of the climatic cabinet. The climatic cabinet also has a gas supply device, whose at least one gas exhaust opening is situated in such a way that the cross-section of the loading opening is covered by a gas curtain, in the area of the gas exhaust openings when gas is supplied.

18 Claims, 4 Drawing Sheets

CLIMATIC CABINET AND, IN PARTICULAR, A CLIMATIC COOLING CABINET

FIELD OF THE INVENTION

The invention concerns a climatic cabinet and, in particular, a climatic cooling cabinet. Climatic cabinets are usually used to keep specimens under defined climatic conditions, such as at a defined temperature or in an atmosphere of defined composition. Examples of climatic cabinets are warming cabinets, cooling cabinets, or incubators, in which cell cultures or microorganisms are stored at elevated temperatures and with very high air humidity and perhaps, in a carbon dioxide-enriched atmosphere, for a longer period of time. The specimens are generally placed on suitable specimen slides, such as microtiter plates. To hold the specimen slides, one or more holding racks are usually situated in the climatized interior of the climatic cabinet. The holding racks are stored, either stationary or rotatable (so-called carousel), in the interior.

BACKGROUND OF THE INVENTION

The interior of the climatic cabinet is, as a rule, accessible through a door, which is large enough, so as to set up a holding rack in the interior and to take it out of the interior. Furthermore, the interior can be cleaned and maintained through the door.

The holding rack is preferably loaded with specimen slides automatically with the aid of a suitable transporting device. Since the opening of the large main door would lead to sensitive disturbances of the climatic conditions in the interior, it has been proposed that a separate air lock be used for the loading and unloading of the specimen slides, which has the smallest possible passage cross-section and is only just large enough, so as to bring the specimen slides into the interior with the aid of the transporting device and to bring them out from the interior. Since only a very small opening in the outer wall of the climatic cabinet must be unblocked for the transporting of the specimen slides back and forth, the effects on the climatic conditions in the interior are clearly less and a continuous operation of the climatic cabinet without serious disturbances of the climate in the interior is possible.

Such a device is described, for example, in WO 98/05753 A1. The climatic cabinet described there has, in addition to a main door in the opposite, back wall, another smaller opening, which is used to transport specimen slides in and out of the interior. The smaller back opening, which is designated as a window opening, can be closed with a door. One or more carousels are used as a holding rack for the specimen slides in the interior of the climatic cabinet.

By using the reduced window opening in transporting specimen slides into the climatic chamber or out of it, the effects of the outside atmosphere on the interior can be clearly reduced, but not completely eliminated. Thus, when the small window is opened, there is also a certain exchange of the atmosphere and an influence on the temperature. Usually, that is the limit to the disturbance. In some special cases, however, there may be an impairment of the climate in the interior of the climatic cabinet. If, for example, the climatic cabinet is used as a climatic cooling cabinet, a small quantity of moisture is dragged in from the surrounding atmosphere into the interior of the climatic chamber every time a specimen slide is transported in. The moisture accumulates gradually in the interior and condenses or freezes because of the reduced temperature in the interior. If the moisture on specimen slides condenses or freezes, then this can lead to damage to the microorganisms or cell cultures and to a contamination of the specimens.

U.S. Pat. No. 6,467,285 B2 describes a climatic cooling cabinet, which is very similar to the apparatus of WO 98/05753 A1. The climatic cooling cabinet has a carousel to hold specimen slides in its interior, which are automatically transported into the interior with a transporting device and again conveyed out of it. Also, the transport does not take place here through the main door of the climatic cabinet, but rather through a smaller transporting air lock. There is a difference from WO 98/05753 A1 here, however, in that the air lock is constructed as a chamber, which can be closed on both sides, both with respect to the interior of the climatic cabinet and to its outside and which can be climatized itself alone. In order to move a specimen slide into the interior of the apparatus, the outer door of the air lock chamber is first opened, and the specimen slide is pushed into the air lock chamber while the inner door of the air lock chamber is closed. Then, the outer door of the air lock chamber is also closed, and a dry gas is introduced into the air lock chamber from a single inlet, which empties into an upper, inner section of the chamber, so as to expel the moisture from the air lock chamber and cool it. Subsequently, the inner door of the air lock chamber is opened, and the specimen slide is transported from the air lock chamber to the carousel and laid there. To transport the specimen slide from the climatic cooling cabinet, the steps are carried out in the reverse sequence. By means of the measures described, the influence on the climate in the interior of the climatic cooling cabinet by the outside atmosphere is reduced even more than in the case of WO 98/05753 A1. The apparatus, however, is constructed in a rather complicated manner and the transporting of each specimen slide takes a relatively long time, since the specimen slide must spend a longer period of time in the air lock chamber, until the dry gas has completely displaced the atmosphere in the air lock chamber.

SUMMARY OF THE INVENTION

Therefore, as in the past, there is a need for a climatic cabinet, in particular, for a climatic cooling cabinet, which is simply constructed and nevertheless, reliably prevents an impairment of the climatic conditions in the interior by the effects of the outer atmosphere. The problem of the invention is correspondingly, to specify such an apparatus.

This problem is solved with the climatic cabinet in accordance with Claim 1. Further refinements and preferred embodiments can be deduced from the dependent claims.

Therefore, the invention concerns a climatic cabinet of the type described in the beginning, in which the transporting of the specimen slide takes place through a separate loading opening, which is adapted, in its size, to the dimensions of the specimen slide. The loading opening is therefore only as large as is necessary so as to convey a specimen slide, by means of the transporting device provided for the purpose, into the interior or out of it. The climatic cabinet, in accordance with the invention, can, therefore, basically be constructed like climatic cabinets known in the state of the art and differs from them, essentially only in the construction in the area of the loading opening and here, in particular, the gas supply device.

The invention is thereby based on the finding that a transporting air lock, closed on both sides, as described in U.S. Pat. No. 6,467,285 B2, and a complete exchange of the atmosphere in the transporting air lock is not required, if an impairment of the conditions in the interior of a climatic cabinet is to be prevented, but rather merely a loading opening which can be closed to the outside is sufficient, if provision is made for a suitable guiding of the gas flow in the area of the loading opening.

In the climatic cabinet, in accordance with the invention, the gas supply device therefore has at least one gas exhaust opening, which is located in the area of the loading opening in such a way that when the gas is being supplied, the cross-section of the loading opening is covered by a gas curtain in the area of the gas exhaust openings. The gas curtain thus produced practically completely closes the cross-section of the loading opening against the penetration of surrounding air and thus reliably prevents an impairment of the climate in the interior of the climatic cabinet by the surrounding atmosphere. This prevents, at the same time, moisture from entering the climatic chamber with the surrounding air and from being condensed there. In this respect, the gas curtain replaces the inner transport air lock door of U.S. Pat. No. 6,467,285 B2 and thus simplifies the construction of the apparatus. On the other hand, the gas curtain can be passed readily by the transporting apparatus with the specimen slide, without a longer residence time in the loading opening, its closing on both sides and a complete gas exchange in the loading opening being required. In this way, it is possible to accelerate the transporting.

As long as the placement site and opening size are ensured, the at least one gas exhaust opening can basically be located anywhere in the area of the loading opening such that the opening cross-section of the loading opening is completely covered by the gas flow. A slit nozzle, for example, can serve as the gas exhaust opening. Alternately, several small nozzles can be used to cover the opening cross-section.

It has proved expedient to place at least one gas exhaust opening in the area of the entry of the loading opening, pointing outwards, so as to protect the loading opening as completely as possible from the penetration of surrounding air and the entrainment of moisture. This does not rule out the possibility, however, that gas exhaust openings are present, exclusively or additionally, in the inside area of the loading opening.

It is conceivable, for example, to locate the gas exhaust openings outside the loading opening in the area bordering the inner end of the opening, so that the outflow openings of the gas exhaust openings point in the direction of its outer opening. The gas flow then passes the loading opening from the interior, in the direction of the outer end. It is preferable, however, to locate the gas exhaust openings in the area of the loading opening and more precisely, in the area of the loading opening walls, which define the loading opening. The length of the loading opening is usually determined by the thickness of the sidewalls, which surround the interior of the climatic cabinet. However, it is also possible to prolong the loading opening beyond the thickness of the sidewalls and to allow the loading opening walls to protrude into the interior of the climatic cabinet, or preferably, beyond the exterior of the climatic cabinet.

A gas curtain, covering the cross-section of the loading opening can be attained in a particularly reliable manner if several gas exhaust openings are used to set up the gas curtain. For example, gas exhaust openings can be opposite one another, on opposing sides of the loading opening. They can be, for example, opposing sidewalls of the loading opening. This arrangement has the advantage that when using microtiter plates or similar specimen slides with openly preserved liquid samples, gas is not blown directly on the sample. However, the arrangement of the gas exhaust openings in the ceiling and floor walls of the loading opening—exclusively there or in addition to the sidewalls—is also possible.

The number of gas exhaust openings depends on the size of the loading opening and should be sufficient in any case, so as to guarantee a gas flow which prevents the penetration of surrounding air from the outside area of the climatic cabinet into the loading opening. It may be appropriate to place several rows of gas exhaust openings in the loading opening. A high number of gas exhaust openings per area can be attained, for example, by a staggered arrangement of the gas exhaust openings.

It may also be sensible to purposefully set the flow direction of the gas exhaust openings. For example, it is possible to align at least some of the gas exhaust openings, inclined, in the direction of the exterior of the climatic cabinet. In this way, a gas flow is produced in the direction of the outer entry of the loading opening, and away from this, and the penetration of surrounding air is also made difficult. For this, it is not basically necessary that all gas exhaust openings be oriented in the direction of the outside of the loading opening, but at present, this is preferred.

When placing a larger number of gas exhaust openings in the walls of the loading opening, it may be sensible for a uniform and simple supply of the gas to surround the loading opening with a chamber, at least in the areas in which the openings are present, wherein the chamber is filled with the gas and from which the gas then arrives at the gas exhaust openings connected with the gas collecting chamber. Thus, only one single gas supply line, discharging into the gas collecting chamber, is necessary.

In addition to or instead of placing the gas exhaust openings in the loading opening, at least one gas exhaust opening can also be provided outside the loading opening, adjacent to the entry of the loading opening, pointing to the outside. As already in the case of the gas exhaust openings in the walls of the loading opening, it is also possible, in this case, for gas exhaust openings to be present on both sides, completely or partially around the loading opening. For the reasons already mentioned in the preceding, it may be expedient to place the gas exhaust openings so that a direct gas effect on the samples is avoided.

Another placement site for at least one of the gas exhaust openings is the door which closes the loading opening on the front side. One particular possibility with sliding doors is to place one or more gas exhaust openings on the side of the door, which, upon opening, is pushed beyond the entry of the loading opening and when open, comes to lie adjacent to the loading opening.

As already in the case of the gas exhaust openings located in the loading opening, the gas exhaust openings present outside, before the loading opening, can be oriented in such a way that gas flows out, at an incline, away from the climatic cabinet.

As a gas, basically any suitable gas, with respect to the atmosphere present in the interior of the climatic cabinet, can be used. Essentially anhydrous gases and/or inert gases (protective gases) are preferably used, for example, dried air, nitrogen, or carbon dioxide. At present, nitrogen is preferred. This has the advantage that nitrogen conduits, usually present in laboratories, can be used, perhaps using a reducing valve, which reduces the pressure to a suitable preliminary pressure of, for example, 1 bar.

In order to adapt the gas to the temperature of the interior, the gas supply conduit can be conducted through the climatized interior and/or through the heat exchanger section of the apparatus for the tempering of the gas.

Furthermore, it is possible to use the gas also to influence the atmosphere in the interior of the climatic cabinet. It is sensible, for example, if an inert gas, such as nitrogen, is used as the gas and air-sensitive specimens are stored in the interior. On the one hand, it is conceivable to branch off a supply line for the interior from the gas supply line for the loading opening, and to provide the interior with gas in this manner. On the other hand, or perhaps also as a supplementary measure, a provisioning of the interior with gas can take place via the loading opening. For a sufficient gas provisioning of the interior, it may then be sensible to prolong the gas supply of the loading opening beyond the period which would be required to protect the climatic cabinet during the loading and unloading with specimen slides, and to supply the loading opening with gas, for example, without interruption.

On the other hand, however, it may also be sensible to couple the gas supply to the opening of the door, which closes the loading opening. For this purpose then, a control device is present in the climatic cabinet, in accordance with the invention, which controls a control valve in the gas supply device in such a manner that the opening and closing of the control valve—and thus the turning on and off of the gas supply into the loading opening—depends on whether the door which closes the loading opening is open or closed. Appropriately, the control valve is opened and gas flows in, if the door before the loading opening is opened. Alternately, the gas supply can also begin shortly before the opening of the door. After the closing of the door, the control valve is also closed, and the gas supply is ended. For these control functions, a separate control device does not have to be provided, but rather the functions can be integrated into a control device, which, in any case, is usually already present in a climatic cabinet and, for example, controls the transporting device for the loading and unloading of the specimen slide or regulates the temperature in the climatic cabinet. Appropriately, this control device controls the automatic opening and closing of the door, which closes the loading opening.

The quantity of the gas supply into the loading opening depends, among other factors, on the size of the opening, the number of gas exhaust openings which supply gas to the opening, and the climatic conditions in the interior of the climatic cabinet and in the surroundings of the climatic cabinet. The gas supply should be set sufficiently high, so as to prevent a penetration of surrounding air into the loading opening. It may be sensible therein to construct the control device so that the gas supply is regulated as a function of the climatic conditions in the interior, on the one hand, and in the outside space around the climatic cabinet, on the other hand. It is particularly expedient here to observe the temperature difference between the interior and the outside surroundings of the climatic cabinet. If, for example, the temperature in the interior of the climatic cabinet is clearly lower than in the outside surroundings of the climatic cabinet, the danger is particularly great that moisture will penetrate into the interior and condense there. In case of a climatic cooling cabinet, therefore, it may be sensible to increase the gas supply with an increasing temperature difference.

BRIEF DESCRIPTION OF THE DRAWINGS

The invention will be explained in more detail below, with the aid of a drawing. The figures schematically show the following.

DETAILED DESCRIPTION OF THE INVENTION

Figure 1:
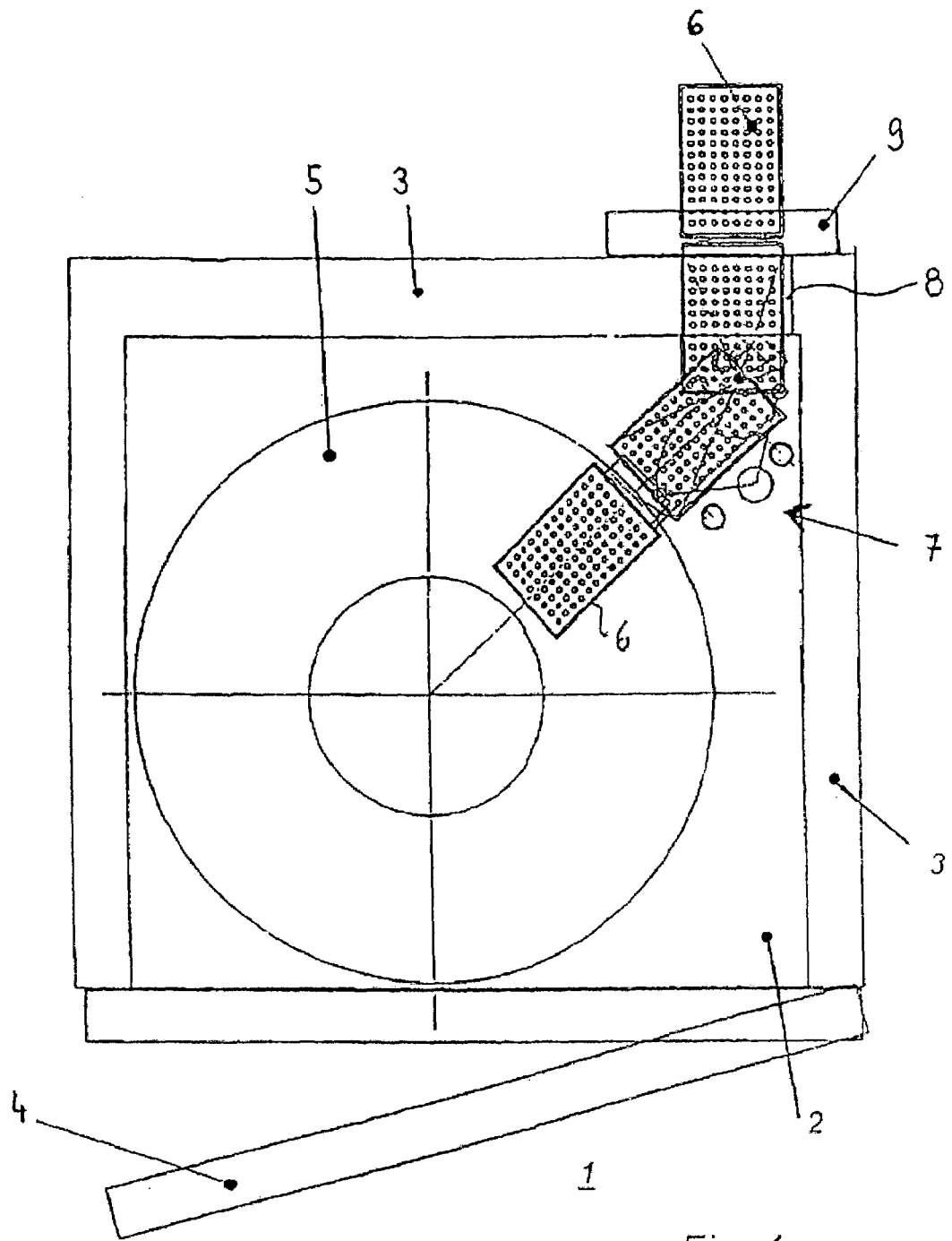
FIG. 1, a climatic cabinet, in accordance with the invention, in cross-section.

The climatic cabinet 1, shown in FIG. 1, has an interior 2, which is surrounded by sidewalls 3 and can be closed with a door 4, which opens manually. This door 4, designated below as the main door, which is shown both closed and half-opened, takes up, with regard to its size, essentially the entire front side of the climatic cabinet 1. A holding rack, in the form of a carousel 5, which pivots and in which a large number of specimen slides can be stored, is set up in the interior 2. For the loading and unloading of the specimen slides 6, a transporting device 7 is present in the back area of the climatic cabinet 1 (to the right, above, in FIG. 1). The transporting takes place through a loading opening 8 in the back wall of the climatic cabinet 1. The size of the loading opening 8 is adapted to the size of the specimen slides 6 and is just large enough so that the specimen slide 6 can be transported through the loading opening 8 with the transporting device 7. The outer side of the loading opening 8 can be closed tightly with a door 9, which opens and shuts automatically. The opening and shutting of the door 9 take place in a manner coordinated with the transporting device 7 via a control device, which is not depicted here. Various transporting stages of a single specimen slide 6 from outside the climatic cabinet into the carousel 5 are indicated by indicating four transporting stages of the specimen slide. The depicted climatic cabinet 1 corresponds essentially to that described in WO 98/05753 A1. It differs from this, however, in the development of the loading opening 8.

In the example of the inventive climatic cabinet shown, gas exhaust openings are situated in the loading opening 8, which openings conduct a gas, here nitrogen, to the loading opening. The gas exhaust openings are not given in FIG. 1, but are depicted in FIG. 2 and are designated by reference symbol 10.

Figure 2:
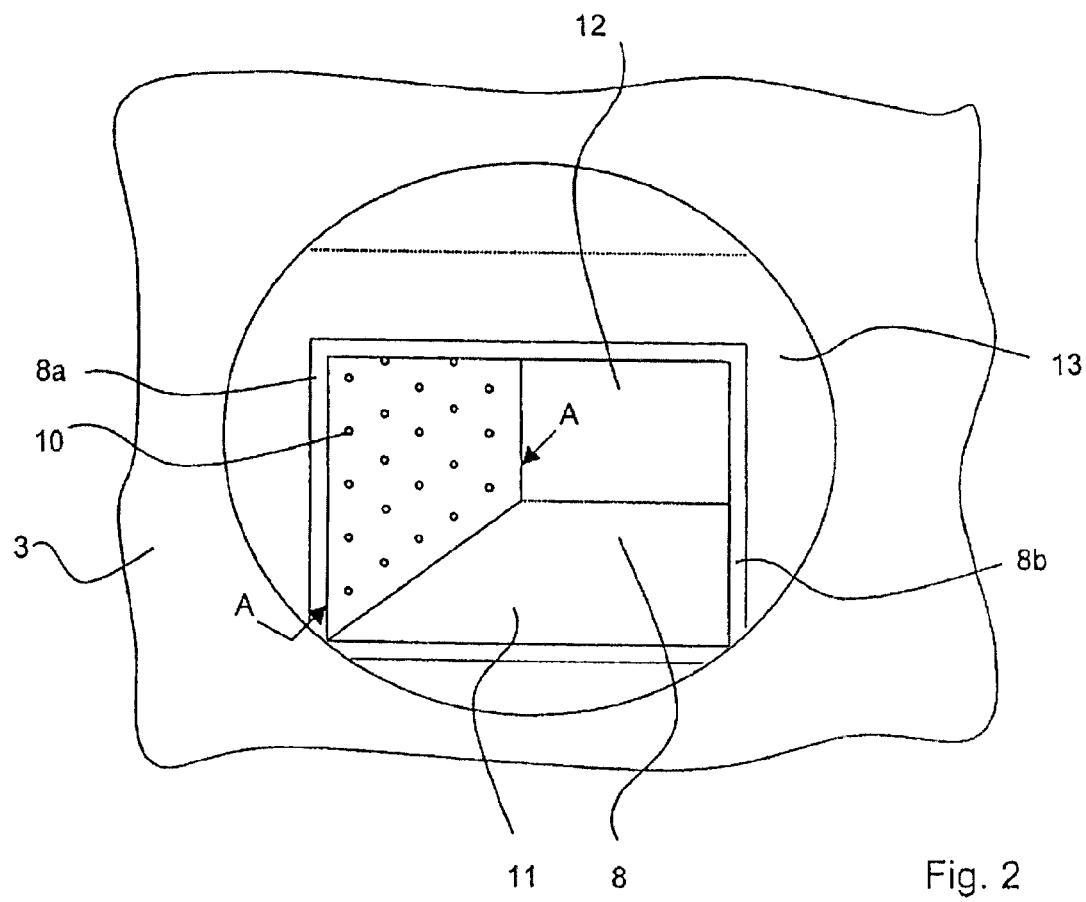
FIG. 2, a top view of the loading opening of the climatic cabinet shown in FIG. 1, seen from outside the climatic cabinet.

FIG. 2 is a top view of the loading opening 8 and the back wall 3 (in FIG. 1, the upper wall), seen from outside the climatic cabinet 1. The door 9, which closes the outer entry 11 of the loading opening 8, is not depicted in FIG. 2. Likewise, the transporting device 7 and specimen slide 6 are omitted for the sake of clarity. The latter correspond to the state of the art.

In contrast to the state of the art, however, gas exhaust openings 10 are provided in the interior of the loading opening 8, so as to produce a gas curtain, which covers the cross-section of the loading opening 8. As can be seen in the left part of FIG. 2, 5 rows of 5 gas exhaust openings each are uniformly present in the area of the left sidewall 8a, distributed over its surface. These gas exhaust openings 10 go through the sidewall 8a and open into a gas collecting chamber 13, which surrounds the loading opening 8 and is made evident by the dotted line and which is provided with gas via a gas connection. This gas collecting chamber 13 is used for setting up a preliminary gas pressure and uniform distribution of the gas.

On the side opposite the wall, gas discharge openings are also present in wall 8b as in wall 8a. A broad gas curtain, which covers the entire opening cross-section of the loading opening 8, can be produced over the entire length of the loading opening 8 from the inner entry 12 at the side of the interior 2 to the Outer entry at the outside of the climatic cabinet by the uniform distribution of the gas discharge openings 10 in the area of the loading opening sidewalls 8a and 8b, which surround the loading opening 8. In this way, the penetration of surrounding air into the interior 2 can be reliably prevented, without a door to close the inner entry 12 being necessary, as is described in U.S. Pat. No. 6,467,285 B2.

Figure 3:
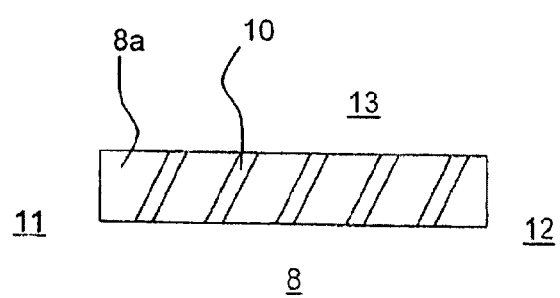
FIG. 3, a cross-section through a sidewall of the loading opening, along the line A—A in FIG. 2.

FIG. 3 shows a preferred arrangement of the gas exhaust openings 10 in one of the walls of the loading opening 8, here, for example, side wall 8a. The cross-section through the wall 8a along line A—A makes clear that all gas exhaust openings run, at an incline, with their openings pointing to the loading opening 8, in the direction of the outer opening 11. Thus, a gas flow, which is directed from the loading opening 8, in the direction of the outer opening 11, is produced. In this way, a penetration of the surrounding air through the opening 11 into the loading opening 8 can be prevented in a particularly reliable manner.

Figure 4:
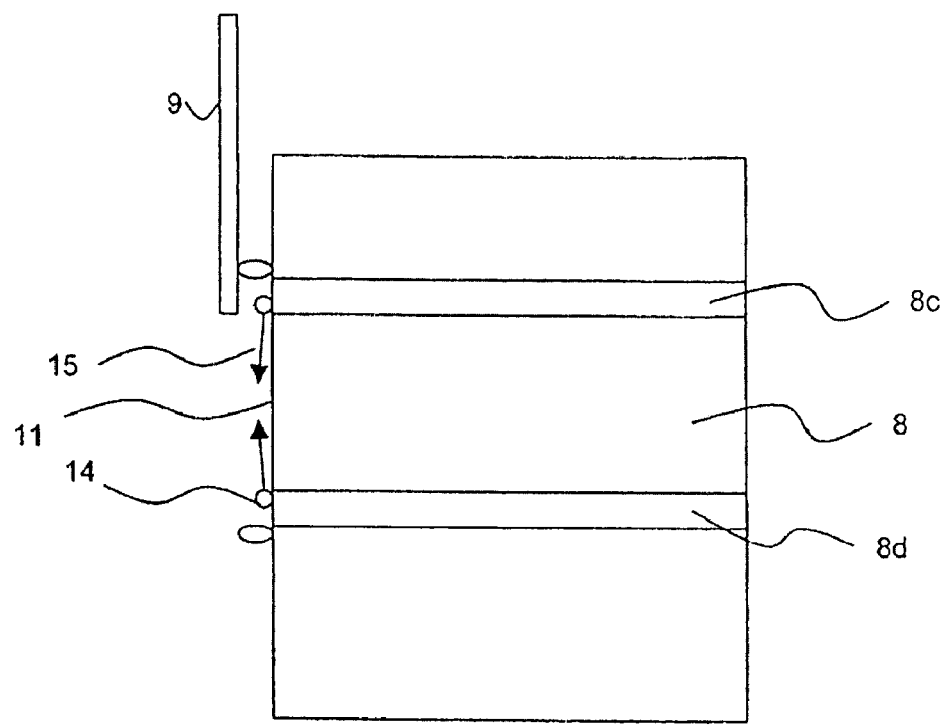
FIG. 4, another example of a climatic cabinet, in accordance with the invention, in the cross-section in the area of the loading opening.

FIG. 4 illustrates another embodiment of the invention, in which a gas curtain is produced on the outside of the loading opening 8. For this purpose, two gas distribution tubes 14 are located above and below the outer entry 11, here from the upper wall 8c and the lower wall 8d of the loading opening 8. Distributed uniformly over their length, the gas distribution tubes have gas exhaust openings 10, which are oriented in the direction of the entry 11 (see FIG. 5)—here in such a way that the gas flow 15 is directed away from the entry 11 to the outside.

Figure 5:
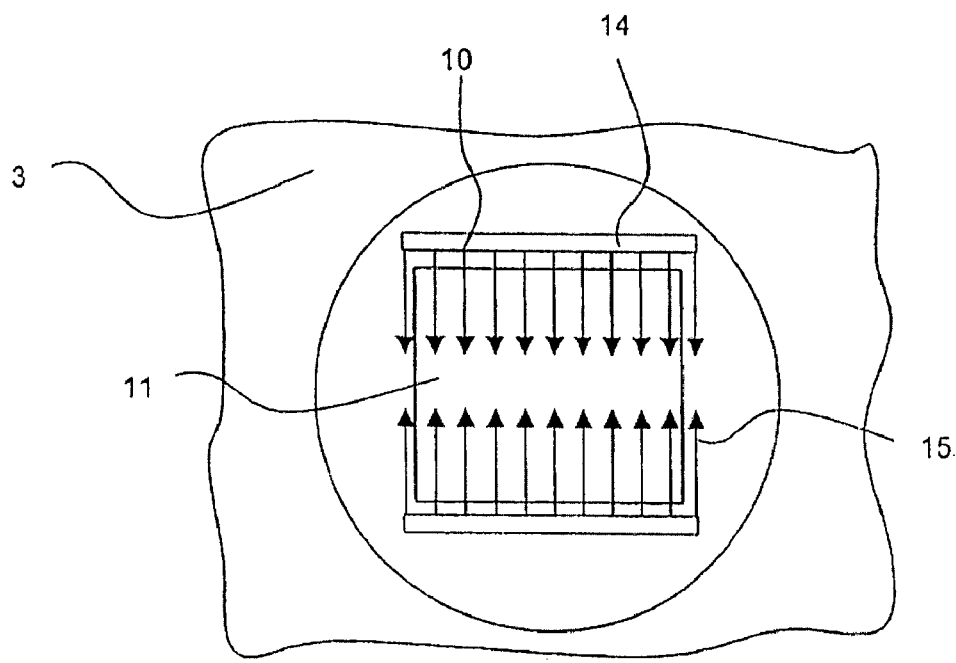
FIG. 5, a top view of the loading opening, according to FIG. 4.
Figure 6:
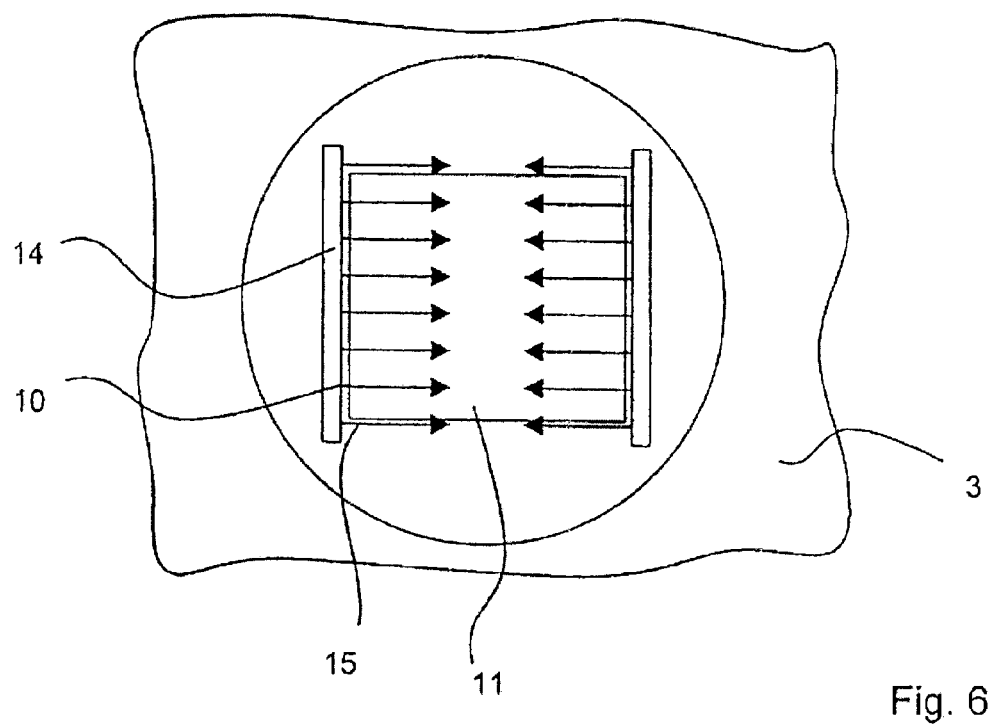
FIG. 6, an alternative embodiment for the embodiment according to FIG. 5, also in top view.

FIG. 6 shows an alternative for the arrangement of the gas distribution tubes in FIG. 5. Here, the gas distribution tubes 14 are located to the right and to the left of the outer entry 11. This has the advantage that a specimen slide is not hit by the gas flow 15, from above, during the transporting, which can be disadvantageous with specimen slides exposed on top, such as microtiter plates with openly stored samples.

A combination of both embodiments according to FIG. 5 and FIG. 6 to form a loading opening, which is surrounded on all sides by gas exhaust openings, is, of course, also possible.

The invention claimed is:

1. A climatic cabinet, comprising:
 an interior having a holding rack configured to hold specimen slides;
 an automatic transporting device configured to load and unload the holding rack with the specimen slides;
 a loading opening for transporting the specimen slides between the interior and an exterior of the cabinet during loading and unloading thereof, said loading opening having an interior face and an exterior face, wherein said loading opening is located in a cabinet sidewall, and has dimensions substantially conforming to the specimen slides;
 a door adapted to tightly seal said loading opening; and
 a gas supply system for supplying a flow of a gas proximate said loading opening, wherein said gas supply system comprises at least one gas exhaust opening proximate said loading opening configured to cover a cross-section of the loading opening with a gas curtain.

2. The climatic cabinet of claim 1, wherein said at least one gas exhaust opening is provided proximate the exterior face of said loading opening.

3. The climatic cabinet of claim 1, wherein said at least one gas exhaust opening discharges into said loading opening.

4. The climatic cabinet of claim 3, wherein gas exhaust openings are provided in one or more pairs of opposing walls surrounding said loading opening.

5. The climatic cabinet of claim 3, further comprising several rows of gas exhaust openings arranged one behind another.

6. The climatic cabinet of claim 3, wherein at least one gas exhaust opening is inclined towards the exterior of said cabinet.

7. The climatic cabinet of claim 3, further comprising a gas collecting chamber surrounding said loading opening, said gas collecting chamber being linked with said at least one gas exhaust opening and connected to a gas supply conduit.

8. The climatic cabinet of claim 7, wherein said gas supply conduit conducts the gas through at least one of the interior of the climatic cabinet and a heat exchanger area of the climatic cabinet.

9. The climatic cabinet of claim 1, wherein the gas is nitrogen.

10. The climatic cabinet of claim 1, wherein said at least one gas exhaust opening is located adjacent the exterior face of said loading opening.

11. The climatic cabinet of claim 10, wherein gas exhaust openings are provided along at least one set of opposing pairs of sides of said loading opening adjacent the exterior face thereof.

12. The climatic cabinet of claim 1, wherein at least one gas exhaust opening is provided in said door.

13. The climatic cabinet of claim 1, wherein said at least one gas exhaust opening is angled away from said climatic cabinet.

14. The climatic cabinet of claim 1, further comprising a control device for controlling a control valve in said gas supply system, and wherein said gas supply system is responsive to opening and closing of said door.

15. The climatic cabinet of claim 14, wherein said control device activates said gas flow at one of during and just prior to opening of said door and deactivates said gas flow after said door is closed.

16. The climatic cabinet of claim 14, wherein said control device regulates said gas flow as a function of a temperature difference between the interior and exterior of said climatic cabinet.

17. The climatic cabinet of claim 1, wherein said door comprises an automatically opening and closing door.

18. The climatic cabinet of claim 1, wherein said climatic cabinet comprises a cooling cabinet.

* * * * *